(12) United States Patent
Olsen et al.

(10) Patent No.: US 6,303,752 B1
(45) Date of Patent: *Oct. 16, 2001

(54) POLYPEPTIDES CONJUGATED WITH POLYMERS

(75) Inventors: Arne Agerlin Olsen, Virum; Tine Muxoll Fatum, Allerød; Heinz Josef Deussen, Søborg; Erwin Ludo Roggen, Lyngby, all of (DK)

(73) Assignee: Novozymes A/S, Bagsvaerd (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/104,623

(22) Filed: Jun. 25, 1998

Related U.S. Application Data

(60) Provisional application No. 60/051,830, filed on Jul. 7, 1997.

(30) Foreign Application Priority Data

Jun. 25, 1997 (DK) .................................................. 0753/97

(51) Int. Cl.[7] ............................... C07K 1/10; C12N 9/00; C12N 9/02; C12N 9/54; C12N 9/56
(52) U.S. Cl. ...................... 530/350; 530/402; 530/403; 435/189; 435/193; 435/221; 435/222
(58) Field of Search ..................................... 530/350, 402, 530/403; 435/189, 193, 221, 222

(56) References Cited

U.S. PATENT DOCUMENTS

| | | | |
|---|---|---|---|
| 3,910,825 | 10/1975 | Hüper et al. ............................ | 435/44 |
| 4,179,337 | 12/1979 | Davis et al. ........................... | 435/181 |
| 4,640,835 | 2/1987 | Shimizu et al. .................... | 424/94.63 |
| 5,492,821 | * 2/1996 | Callstrom et al. ..................... | 345/188 |
| 5,661,020 | * 8/1997 | Snow et al. ............................ | 435/166 |
| 5,808,096 | * 9/1998 | Zaplisky ................................ | 548/520 |
| 5,840,844 | * 11/1998 | Lasky et al. .......................... | 530/350 |
| 5,856,451 | * 1/1999 | Olsen et al. ........................... | 530/402 |
| 5,932,462 | * 8/1999 | Harris et al. .......................... | 435/188 |

FOREIGN PATENT DOCUMENTS

| | | |
|---|---|---|
| 0 256 127 | 2/1988 | (EP) . |
| 0 418 625 | * 3/1991 | (EP) . |
| WO 94/06907 | * 3/1994 | (WO) . |
| WO 96/17929 | 6/1996 | (WO) . |

OTHER PUBLICATIONS

Zaplisky, S., Advanced Drug Delivery Reviews, vol. 16, "Chemistry of polyethylene glycol conjugates with biologically active molecules", pp. 157–182, 1995.*

* cited by examiner

*Primary Examiner*—Ponnathapu Achutamurthy
*Assistant Examiner*—William W. Moore
(74) *Attorney, Agent, or Firm*—Elias J. Lambiris Esq

(57) ABSTRACT

The present invention relates to modified polypeptides with reduced respiratory allergenicity having polymeric molecules with a molecular weight from 100 up to 750 Da, coupled covalently to the parent polypeptide having a molecular weight from 5 to 100 kDa. The present invention also relates to industrial compositions comprising modified polypeptide with reduced respiratory allergenicity, skin care products, the use of modified polypeptides for reducing the allergenicity of industrial composition and products and finally a method for reducing the allergenicity of polypeptides.

32 Claims, No Drawings

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 840 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
      (B) STRAIN: Bacillus sp. PD498, NCIMB No. 40484

(ix) FEATURE:
      (A) NAME/KEY: CDS
      (B) LOCATION:1..840

(xi) SEQUENCE DESCRIPTION: SEQ ID NO: 1:

```
TGG TCA CCG AAT GAC CCT TAC TAT TCT GCT TAC CAG TAT GGA CCA CAA        48
Trp Ser Pro Asn Asp Pro Tyr Tyr Ser Ala Tyr Gln Tyr Gly Pro Gln
 1               5                  10                  15
```

```
AAC ACC TCA ACC CCT GCT GCC TGG GAT GTA ACC CGT GGA AGC AGC ACT      96
Asn Thr Ser Thr Pro Ala Ala Trp Asp Val Thr Arg Gly Ser Ser Thr
             20                  25                  30

CAA ACG GTG GCG GTC CTT GAT TCC GGA GTG GAT TAT AAC CAC CCT GAT     144
Gln Thr Val Ala Val Leu Asp Ser Gly Val Asp Tyr Asn His Pro Asp
             35                  40                  45

CTT GCA AGA AAA GTA ATA AAA GGG TAC GAC TTT ATC GAC AGG GAC AAT     192
Leu Ala Arg Lys Val Ile Lys Gly Tyr Asp Phe Ile Asp Arg Asp Asn
 50                  55                  60

AAC CCA ATG GAT CTT AAC GGA CAT GGT ACC CAT GTT GCC GGT ACT GTT     240
Asn Pro Met Asp Leu Asn Gly His Gly Thr His Val Ala Gly Thr Val
 65                  70                  75                  80

GCT GCT GAT ACG AAC AAT GGA ATT GGC GTA GCC GGT ATG GCA CCA GAT     288
Ala Ala Asp Thr Asn Asn Gly Ile Gly Val Ala Gly Met Ala Pro Asp
                 85                  90                  95

ACG AAG ATC CTT GCC GTA CGG GTC CTT GAT GCC AAT GGA AGT GGC TCA     336
Thr Lys Ile Leu Ala Val Arg Val Leu Asp Ala Asn Gly Ser Gly Ser
                100                 105                 110

CTT GAC AGC ATT GCC TCA GGT ATC CGC TAT GCT GCT GAT CAA GGG GCA     384
Leu Asp Ser Ile Ala Ser Gly Ile Arg Tyr Ala Ala Asp Gln Gly Ala
            115                 120                 125

AAG GTA CTC AAC CTC TCC CTT GGT TGC GAA TGC AAC TCC ACA ACT CTT     432
Lys Val Leu Asn Leu Ser Leu Gly Cys Glu Cys Asn Ser Thr Thr Leu
            130                 135                 140

AAG AGT GCC GTC GAC TAT GCA TGG AAC AAA GGA GCT GTA GTC GTT GCT     480
Lys Ser Ala Val Asp Tyr Ala Trp Asn Lys Gly Ala Val Val Val Ala
145                 150                 155                 160

GCT GCA GGG AAT GAC AAT GTA TCC CGT ACA TTC CAA CCA GCT TCT TAC     528
Ala Ala Gly Asn Asp Asn Val Ser Arg Thr Phe Gln Pro Ala Ser Tyr
                165                 170                 175

CCT AAT GCC ATT GCA GTA GGT GCC ATT GAC TCC AAT GAT CGA AAA GCA     576
Pro Asn Ala Ile Ala Val Gly Ala Ile Asp Ser Asn Asp Arg Lys Ala
            180                 185                 190

TCA TTC TCC AAT TAC GGA ACG TGG GTG GAT GTC ACT GCT CCA GGT GTG     624
Ser Phe Ser Asn Tyr Gly Thr Trp Val Asp Val Thr Ala Pro Gly Val
            195                 200                 205

AAC ATA GCA TCA ACC GTT CCG AAT AAT GGC TAC TCC TAC ATG TCT GGT     672
Asn Ile Ala Ser Thr Val Pro Asn Asn Gly Tyr Ser Tyr Met Ser Gly
210                 215                 220

ACG TCC ATG GCA TCC CCT CAC GTG GCC GGT TTG GCT GCT TTG TTG GCA     720
Thr Ser Met Ala Ser Pro His Val Ala Gly Leu Ala Ala Leu Leu Ala
225                 230                 235                 240

AGT CAA GGT AAG AAT AAC GTA CAA ATC CGC CAG GCC ATT GAG CAA ACC     768
Ser Gln Gly Lys Asn Asn Val Gln Ile Arg Gln Ala Ile Glu Gln Thr
                245                 250                 255

GCC GAT AAG ATC TCT GGC ACT GGA ACA AAC TTC AAG TAT GGT AAA ATC     816
Ala Asp Lys Ile Ser Gly Thr Gly Thr Asn Phe Lys Tyr Gly Lys Ile
            260                 265                 270

AAC TCA AAC AAA GCT GTA AGA TAC                                     840
Asn Ser Asn Lys Ala Val Arg Tyr
            275                 280

(2) INFORMATION FOR SEQ ID NO: 2:

(i) SEQUENCE CHARACTERISTICS:
        (A) LENGTH: 280 amino acids
        (B) TYPE: amino acid
        (D) TOPOLOGY: linear (ii) MOLECULE TYPE: protein (xi) SEQUENCE DESCRIPTION: SEQ ID NO: 2:
```

-continued

```
Trp Ser Pro Asn Asp Pro Tyr Tyr Ser Ala Tyr Gln Tyr Gly Pro Gln
  1               5                  10                  15

Asn Thr Ser Thr Pro Ala Ala Trp Asp Val Thr Arg Gly Ser Ser Thr
             20                  25                  30

Gln Thr Val Ala Val Leu Asp Ser Gly Val Asp Tyr Asn His Pro Asp
         35                  40                  45

Leu Ala Arg Lys Val Ile Lys Gly Tyr Asp Phe Ile Asp Arg Asp Asn
     50                  55                  60

Asn Pro Met Asp Leu Asn Gly His Gly Thr His Val Ala Gly Thr Val
 65                  70                  75                  80

Ala Ala Asp Thr Asn Asn Gly Ile Gly Val Ala Gly Met Ala Pro Asp
                 85                  90                  95

Thr Lys Ile Leu Ala Val Arg Val Leu Asp Ala Asn Gly Ser Gly Ser
            100                 105                 110

Leu Asp Ser Ile Ala Ser Gly Ile Arg Tyr Ala Ala Asp Gln Gly Ala
        115                 120                 125

Lys Val Leu Asn Leu Ser Leu Gly Cys Glu Cys Asn Ser Thr Thr Leu
    130                 135                 140

Lys Ser Ala Val Asp Tyr Ala Trp Asn Lys Gly Ala Val Val Val Ala
145                 150                 155                 160

Ala Ala Gly Asn Asp Asn Val Ser Arg Thr Phe Gln Pro Ala Ser Tyr
                165                 170                 175

Pro Asn Ala Ile Ala Val Gly Ala Ile Asp Ser Asn Asp Arg Lys Ala
            180                 185                 190

Ser Phe Ser Asn Tyr Gly Thr Trp Val Asp Val Thr Ala Pro Gly Val
        195                 200                 205

Asn Ile Ala Ser Thr Val Pro Asn Asn Gly Tyr Ser Tyr Met Ser Gly
    210                 215                 220

Thr Ser Met Ala Ser Pro His Val Ala Gly Leu Ala Ala Leu Leu Ala
225                 230                 235                 240

Ser Gln Gly Lys Asn Asn Val Gln Ile Arg Gln Ala Ile Glu Gln Thr
                245                 250                 255

Ala Asp Lys Ile Ser Gly Thr Gly Thr Asn Phe Lys Tyr Gly Lys Ile
            260                 265                 270

Asn Ser Asn Lys Ala Val Arg Tyr
        275                 280
```

(2) INFORMATION FOR SEQ ID NO: 3:

(i) SEQUENCE CHARACTERISTICS:
(A) LENGTH: 274 amino acids
(B) TYPE: amino acid
(C) STRANDEDNESS: single
(D) TOPOLOGY: linear (ii) MOLECULE TYPE: protein (vi) ORIGINAL SOURCE:
(B) STRAIN: Bacillus sp. variant (xi) SEQUENCE DESCRIPTION: SEQ ID NO: 3:

```
Ala Gln Thr Val Pro Tyr Gly Ile Pro Leu Ile Lys Ala Asp Lys Val
1               5                   10                  15

Gln Ala Gln Gly Tyr Lys Gly Ala Asn Val Lys Val Gly Ile Ile Asp
            20                  25                  30

Thr Gly Ile Ala Xaa Ser His Thr Asp Leu Lys Val Val Gly Gly Ala
        35                  40                  45
```

```
Ser Phe Val Ser Gly Glu Ser Tyr Asn Thr Asp Gly Asn Gly His Gly
    50                  55                  60

Thr His Val Ala Gly Thr Val Ala Ala Leu Asp Asn Thr Thr Gly Val
 65                  70                  75                  80

Leu Gly Val Ala Pro Asn Val Ser Leu Tyr Ala Ile Lys Val Leu Asn
                 85                  90                  95

Ser Ser Gly Ser Gly Thr Tyr Ser Ala Ile Val Ser Gly Ile Glu Trp
                100                 105                 110

Ala Thr Gln Asn Gly Leu Asp Val Ile Asn Met Ser Leu Gly Gly Pro
            115                 120                 125

Ser Gly Ser Thr Ala Leu Lys Gln Ala Val Asp Lys Ala Tyr Ala Ser
    130                 135                 140

Gly Ile Val Val Ala Ala Ala Gly Asn Ser Gly Ser Ser Gly Ser
145                 150                 155                 160

Gln Asn Thr Ile Gly Tyr Pro Ala Lys Tyr Asp Ser Val Ile Ala Val
                165                 170                 175

Gly Ala Val Asp Ser Asn Lys Asn Arg Ala Ser Phe Ser Ser Val Gly
                180                 185                 190

Xaa Glu Leu Glu Val Met Ala Pro Gly Val Ser Val Tyr Ser Thr Tyr
            195                 200                 205

Pro Ser Asn Thr Tyr Thr Ser Leu Asn Gly Thr Ser Met Ala Ser Pro
    210                 215                 220

His Val Ala Gly Ala Ala Ala Leu Ile Leu Ser Lys Tyr Pro Thr Leu
225                 230                 235                 240

Ser Ala Ser Gln Val Arg Asn Arg Leu Ser Ser Thr Ala Thr Asn Leu
                245                 250                 255

Gly Asp Ser Phe Tyr Tyr Gly Lys Gly Leu Ile Asn Val Glu Ala Ala
                260                 265                 270

Ala Gln (2) INFORMATION FOR SEQ ID NO: 4:

(i) SEQUENCE CHARACTERISTICS:
        (A) LENGTH: 433 amino acids
        (B) TYPE: amino acid
        (C) STRANDEDNESS:
        (D) TOPOLOGY: linear (ii) MOLECULE TYPE: protein (vi) ORIGINAL SOURCE:
        (B) STRAIN: Bacillus sp. Y (xi) SEQUENCE DESCRIPTION: SEQ ID NO: 4:

Asn Asp Val Ala Arg Gly Ile Val Lys Ala Asp Val Ala Gln Asn Asn
 1               5                  10                  15

Tyr Gly Leu Tyr Gly Gln Gly Gln Leu Val Ala Val Ala Asp Thr Gly
             20                  25                  30

Leu Asp Thr Gly Arg Asn Asp Ser Ser Met His Glu Ala Phe Arg Gly
         35                  40                  45

Lys Ile Thr Ala Leu Tyr Ala Leu Gly Arg Thr Asn Asn Ala Ser Asp
 50                  55                  60

Pro Asn Gly His Gly Thr His Val Ala Gly Ser Val Leu Gly Asn Ala
 65                  70                  75                  80

Leu Asn Lys Gly Met Ala Pro Gln Ala Asn Leu Val Phe Gln Ser Ile
             85                  90                  95
```

```
Met Asp Ser Ser Gly Gly Leu Gly Leu Pro Ser Asn Leu Asn Thr
            100                 105                 110

Leu Phe Ser Gln Ala Trp Asn Ala Gly Ala Arg Ile His Thr Asn Ser
        115                 120                 125

Trp Gly Ala Pro Val Asn Gly Ala Tyr Thr Ala Asn Ser Arg Gln Val
    130                 135                 140

Asp Glu Tyr Val Arg Asn Asn Asp Met Thr Val Leu Phe Ala Ala Gly
145                 150                 155                 160

Asn Glu Gly Pro Asn Ser Gly Thr Ile Ser Ala Pro Gly Thr Ala Lys
                165                 170                 175

Asn Ala Ile Thr Val Gly Ala Thr Glu Asn Tyr Arg Pro Ser Phe Gly
            180                 185                 190

Ser Ile Ala Asp Asn Pro Asn His Ile Ala Gln Phe Ser Arg Gly
        195                 200                 205

Ala Thr Arg Asp Gly Arg Ile Lys Pro Asp Val Thr Ala Pro Gly Thr
    210                 215                 220

Phe Ile Leu Ser Ala Arg Ser Ser Leu Ala Pro Asp Ser Ser Phe Trp
225                 230                 235                 240

Ala Asn Tyr Asn Ser Lys Tyr Ala Tyr Met Gly Gly Thr Ser Met Ala
                245                 250                 255

Thr Pro Ile Val Ala Gly Asn Val Ala Gln Leu Arg Glu His Phe Ile
            260                 265                 270

Lys Asn Arg Gly Ile Thr Pro Lys Pro Ser Leu Ile Lys Ala Ala Leu
        275                 280                 285

Ile Ala Gly Ala Thr Asp Val Gly Leu Gly Tyr Pro Ser Gly Asp Gln
290                 295                 300

Gly Trp Gly Arg Val Thr Leu Asp Lys Ser Leu Asn Val Ala Tyr Val
305                 310                 315                 320

Asn Glu Ala Thr Ala Leu Ala Thr Gly Gln Lys Ala Thr Tyr Ser Phe
                325                 330                 335

Gln Ala Gln Ala Gly Lys Pro Leu Lys Ile Ser Leu Val Trp Thr Asp
            340                 345                 350

Ala Pro Gly Ser Thr Thr Ala Ser Tyr Thr Leu Val Asn Asp Leu Asp
        355                 360                 365

Leu Val Ile Thr Ala Pro Asn Gly Gln Lys Tyr Val Gly Asn Asp Phe
370                 375                 380

Ser Tyr Pro Tyr Asp Asn Asn Trp Asp Gly Arg Asn Asn Val Glu Asn
385                 390                 395                 400

Val Phe Ile Asn Ala Pro Gln Ser Gly Thr Tyr Ile Ile Glu Val Gln
                405                 410                 415

Ala Tyr Asn Val Pro Ser Gly Pro Gln Arg Phe Ser Leu Ala Ile Val
            420                 425                 430

His
```

(2) INFORMATION FOR SEQ ID NO: 5:

(i) SEQUENCE CHARACTERISTICS:
        (A) LENGTH: 316 amino acids
        (B) TYPE: amino acid
        (C) STRANDEDNESS: single
        (D) TOPOLOGY: linear (ii) MOLECULE TYPE: protein (vi) ORIGINAL SOURCE:
        (B) STRAIN: Bacillus Thermoproteolyticus -continued (xi) SEQUENCE DESCRIPTION: SEQ ID NO: 5:

```
Ile Thr Gly Thr Ser Thr Val Gly Val Gly Arg Gly Val Leu Gly Asp
1               5                   10                  15

Gln Lys Asn Ile Asn Thr Thr Tyr Ser Thr Tyr Tyr Tyr Leu Gln Asp
            20                  25                  30

Asn Thr Arg Gly Asp Gly Ile Phe Thr Tyr Asp Ala Lys Tyr Arg Thr
            35                  40                  45

Thr Leu Pro Gly Ser Leu Trp Ala Asp Ala Asp Asn Gln Phe Phe Ala
            50                  55                  60

Ser Tyr Asp Ala Pro Ala Val Asp Ala His Tyr Tyr Ala Gly Val Thr
65                  70                  75                  80

Tyr Asp Tyr Tyr Lys Asn Val His Asn Arg Leu Ser Tyr Asp Gly Asn
            85                  90                  95

Asn Ala Ala Ile Arg Ser Ser Val His Tyr Ser Gln Gly Tyr Asn Asn
            100                 105                 110

Ala Phe Trp Asn Gly Ser Glu Met Val Tyr Gly Asp Gly Asp Gly Gln
            115                 120                 125

Thr Phe Ile Pro Leu Ser Gly Gly Ile Asp Val Val Ala His Glu Leu
            130                 135                 140

Thr His Ala Val Thr Asp Tyr Thr Ala Gly Leu Ile Tyr Gln Asn Glu
145                 150                 155                 160

Ser Gly Ala Ile Asn Glu Ala Ile Ser Asp Ile Phe Gly Thr Leu Val
            165                 170                 175

Glu Phe Tyr Ala Asn Lys Asn Pro Asp Trp Glu Ile Gly Glu Asp Val
            180                 185                 190

Tyr Thr Pro Gly Ile Ser Gly Asp Ser Leu Arg Ser Met Ser Asp Pro
            195                 200                 205

Ala Lys Tyr Gly Asp Pro Asp His Tyr Ser Lys Arg Tyr Thr Gly Thr
210                 215                 220

Gln Asp Asn Gly Gly Val His Ile Asn Ser Gly Ile Ile Asn Lys Ala
225                 230                 235                 240

Ala Tyr Leu Ile Ser Gln Gly Gly Thr His Tyr Gly Val Ser Val Val
            245                 250                 255

Gly Ile Gly Arg Asp Lys Leu Gly Lys Ile Phe Tyr Arg Ala Leu Thr
            260                 265                 270

Gln Tyr Leu Thr Pro Thr Ser Asn Phe Ser Gln Leu Arg Ala Ala Ala
            275                 280                 285

Val Gln Ser Ala Thr Asp Leu Tyr Gly Ser Thr Ser Gln Glu Val Ala
            290                 295                 300

Ser Val Lys Gln Ala Phe Asp Ala Val Gly Val Lys
305                 310                 315
```

POLYPEPTIDES CONJUGATED WITH POLYMERS

CROSS-REFERENCE TO RELATED APPLICATIONS

This application claims priority under 35 U.S.C. 119 of Danish application 0753/97 filed Jun. 25, 1997, and of U.S. provisional application No. 60/051,830 filed Jul. 7, 1997, the contents of which are fully incorporated herein by reference.

FIELD OF THE INVENTION

The present invention relates to modified polypeptides with reduced respiratory allergenicity, industrial compositions comprising modified polypeptide with reduced respiratory allergenicity, skin care products, the use of modified polypeptides for reducing the allergenicity of industrial composition and products and finally a method for reducing the allergenicity of polypeptides.

BACKGROUND OF THE INVENTION

For both medical and industrial applications the use of polypeptides, including enzymes, are well-known in the art. As polypeptides may potentially cause an undesired immune response—dependent on the way of challenge—typically an IgG and/or IgE response, techniques for reducing it have been developed during the last three decades.

One technique is the "PEGylation" technique where a number of polymeric molecules are coupled to the polypeptide in question. When using this technique the immune system has difficulties in recognizing the epitopes on the polypeptide's surface responsible for the formation of antibodies, thereby reducing the immune response.

For polypeptides introduced directly into the circulatory system of the human body to give a particular physiological effect (i.e. pharmaceuticals) the typical potential immune response is an IgG and/or IgM response, while polypeptides which are inhaled through the respiratory system (i.e. industrial polypeptide) potentially may cause an IgE response (i.e. allergic response).

One of the theories explaining the reduced immune response is that the polymeric molecule(s) shield(s) epitope(s) on the surface of the polypeptide responsible for the immune response leading to antibody formation. Another theory or at least a partial factor is that the heavier the conjugate is, the more reduced immune response is obtained.

U.S. Pat. No. 4,179,337 concerns non-immunogenic polypeptides, such as enzymes and peptide hormones coupled to polyethylene glycol (PEG) or polypropylene glycol (PPG). At least 15% of the polypeptides' physiological activity are maintained. The use of PEG's with a molecular weight in the range from 750 Da to 6,000 Da are exemplified in the patent. The polypeptides are not used for industrial applications.

WO 96/17929 (Novo Nordisk A/S) concerns modified polypeptide conjugates coupled to polymeric molecules such as PEG. The modified enzymes may be used for a number of industrial applications. The molecular weight of the polymeric molecules coupled to the polypeptides in the Examples are 5,000, 15,000 and 35,000 Da, respectively.

SUMMARY OF THE INVENTION

The present invention relates to modified polypeptides with reduced allergenicity and compositions and products for industrial uses comprising modified polypeptide.

It is generally believed that the molecular weight and the length of the polymeric molecules should not be too short/light, as short/light polymeric molecules cannot shield the surface of the polypeptide sufficiently.

This prejudice has now been proven wrong by the inventors for polypeptides, such as enzymes, used for industrial applications, where the polypeptide is not intended to enter the circulatory system.

The present inventors have found that when the polypeptide in question is used for industrial application, where the potential risk is an allergenic response caused by inhalation of the polypeptide, the parent polypeptide may be coupled to polymeric molecules with a molecular weight in the range from 100 Da up to 5,000 Da, preferably from 100 to 2,000 Da, especially 100 to 1,000 Da without loosing the ability to significantly reduce the respiratory allergenic response.

In the first aspect the invention relates to polypeptides coupled to polymeric molecules having a molecular weight from 100 Da to below 750 Da, especially 100 to 500 Da, such as around 300 Da.

In a second aspect the invention relates to compositions for use in industrial products comprising modified polypeptides coupled to polymeric molecules having a molecular weight from 100 Da up to 5,000 Da.

Industrial Polypeptides

Polypeptides used for industrial applications often have an enzymatic and/or anti-microbial activity. Industrial polypeptides are (in contrast to pharmaceutical polypeptides) not intended to be introduced into the circulatory system of the body.

Therefore, it is not very likely that industrial polypeptides, such as enzymes used as active ingredients in industrial compositions and/or products (defined below), such as detergents, including laundry and dish washing detergents, food or feed additives, including additives for bread making, composition for treating textiles, and personal care products, including cosmetics, come into direct contact with the circulatory system of the body of humans or animals, as such polypeptides (or products comprising such polypeptides) are not injected (or the like) into the bloodstream.

Therefore, in the case of the industrial polypeptide the potential risk is respiratory allergy (i.e. IgE response) as a consequence of inhalation of polypeptides through the respiratory passage.

In the context of the present invention "industrial polypeptides" are defined as polypeptides, including peptides, proteins and/or enzymes, which are not intended to be introduced into the circulatory system of the body of humans and/or animals.

Examples of such "Industrial polypeptides" include polypeptides with enzymatic activity as defined below.

The invention also relates to skin care products having reduced allergenicity.

Furthermore, the invention also relates to the use of modified polypeptides with a molecular weight from 100 Da up to 5,000 Da, preferably 100 to 2,000 Da, especially 100 up to 1,000 Da for reducing the allergenicity of industrial products.

Finally the invention relates to a method for reducing the allergenicity of polypeptides by coupling the polypeptide to a polymeric molecule with a molecular weight from 100 Da up to 5,000 Da.

DETAILED DESCRIPTION OF THE INVENTION

The object of the invention is to provide modified polypeptides with reduced allergenicity and compositions and products for industrial uses comprising modified polypeptide with reduced allergenicity.

The term "reduced allergenicity" means in the context of the present invention that the amount of produced IgE (in humans, and molecules with comparable effects in specific animals), which can lead to an allergic state, is decreased when inhaling a modified polypeptide of the invention in comparison to the corresponding parent polypeptide. The term "respiratory allergenicity" may be used instead.

The present inventors have found that when a polypeptide is used for industrial application, where the potential main risk is an allergenic response caused by inhalation of the polypeptide, the parent polypeptide may be coupled to polymeric molecules with a molecular weight in the range from 100 Da up to 5,000 Da, preferably 100 to 2,000 Da, especially 100 to 1,000 Da, without losing the ability to significantly reduce the allergenic response.

In an embodiment of the invention the polymeric molecules coupled to the polypeptide, in particular enzyme, have a molecular weight of from 100 up to 750 Da, such as 100 to 500 Da, such as around 300 Da.

It is surprising that the polymeric molecules coupled to the polypeptide can be as small as this and proves an existing prejudice wrong, i.e. that the molecular weight and the length of the polymeric molecules coupled to the polypeptide should not be too short/light, as short/light polymeric molecules cannot shield the surface of the polypeptide sufficiently.

In the first aspect the invention relates to modified polypeptides having coupled polymeric molecules with a molecular weight from 100 Da up to 750 Da, especially 100 to 500 Da, such as around 300 Da, covalently to the parent polypeptide having a molecular weight between 5 and 100 kDa, such as from 15 to 60 kDa.

It is advantageous to couple short/light polymeric molecules to the polypeptide in question as short/light polymeric molecules have a less tendency to inhibit a functional activity of the polypeptide. For instance, the active site of an enzyme coupled to polymeric molecules having a molecular weight as defined according to the present invention is easier accessible for the substrate in comparison to the corresponding enzyme coupled to larger/heavier polymeric molecules as the spatial hindrance by the polymeric molecules is less pronounced. Further, a polypeptide-polymer conjugate with smaller/lighter polymeric molecules has improved stability in comparison to a corresponding conjugate with larger/heavier polymeric molecules coupled to the polypeptide, as deformation of the polypeptide structure is minimal due to the fact that less weight is pulling the polypeptide structure in different directions.

Another advantage of using small polymeric molecules is that they are cheaper to purchase as polymers are sold per kilo. This reduces the cost of producing a conjugate of the invention.

Assessment of Allergenicity

Allergenicity may be assessed on the basis of inhalation tests, comparing the effect of intratracheally (into the trachea) administrated parent polypeptide with the corresponding modified polypeptide according to the invention.

A number of in vivo animal models exist for assessment of the allergenicity of polypeptides. Some of these models give a suitable basis for hazard assessment in man. Suitable models include a guinea pig model and a mouse model. These models seek to identify respiratory allergens as a function of elicitation reactions induced in previously sensitised animals. According to these models the alleged allergens are introduced intratracheally into the animals.

A suitable strain of guinea pigs, the Dunkin Hartley strain, does not as humans, produce IgE antibodies in connection with the allergic response. However, they produce another type of antibody the IgG1A and IgG1B (see e.g. Prentø, ATLA, 19, p. 8–14, 1991), which are responsible for their allergenic response to inhaled polypeptides including enzymes. Therefore, when using the Dunkin Hartley animal model, the relative amount of IgG1A and IgG1B is a measure of the allergenicity level.

A rat strain suitable for intratracheal exposure to polypeptides, such as enzymes, is the Brown Norway strain. Brown Norway rats produce IgE as the allergic response. Brown Norway rats are used in the trials described in Example 4 and 5 illustrating the invention.

More details on assessing respiratory allergens in guinea pigs and mice is described by Kimber et al.,(1996), Fundamental and Applied Toxicology, 33, p. 1–10.

Other animals such as e.g. rabbits may also be used for comparable studies.

The Polymeric Molecule

The polymeric molecules coupled to the polypeptide may be any suitable polymeric molecule with a molecular weight as defined according to the invention, including natural and synthetic homopolymers, such as polyols (i.e. poly-OH), polyamines (i.e. poly-$NH_2$) and polycarboxyl acids (i.e. poly-COOH), and further heteropolymers i.e. polymers comprising one or more different coupling groups e.g. a hydroxyl group and amine groups.

Examples of suitable polymeric molecules include polymeric molecules selected from the group comprising polyalkylene oxides (PAO), such as polyalkylene glycols (PAG), including polypropylene glycols (PEG), methoxypolyethylene glycols (mPEG) and polypropylene glycols, PEG-glycidyl ethers (Epox-PEG), PEG-oxycarbonylimidazole (CDI-PEG) branched polyethelene glycols (PEGs), polyvinyl alcohol )PVA), polycarboxylates, polyvinylpyrrolidone, poly-D,L-amino acids, polyethylene-co-maleic acid anhydride, polystyrene-co-malic acid arhydride, dextrans including carboxymethyl-dextrans, heparin, homologous albumin, celluloses, including methylcellulose, carboxymethylcellulose, ethylcellulosia, hydroxyethylcellulose carboxyethylcellulose and hydroxypropylcellulose, hydrolysates of chitosan, starches such as hydroxyethyl-starches and hydroxy propyl-starches, glycogen, agaroses and derivatives thereof, guar gum, pullulan, inulin, xanthan gum, carrageenan, pectin, alginic acid hydrolysates and bio-polymers.

Preferred polymeric molecules are non-toxic polymeric molecules such as (m)polyethylene glycol (mPEG) which further requires a relatively simple chemistry for its covalent coupling to attachment groups on the enzyme's surface.

Generally seen polyalkylene oxides (PAO), such as polyethylene oxides, such as PEG and especially mPEG, are the preferred polymeric molecules, as these polymeric molecules, in comparison to polysaccharides such as dextran, pullulan and the like, have few reactive groups capable of cross-linking, which is undesirable.

Even though all of the above mentioned polymeric molecules may be used according to the invention methoxy-polyethylene glycols (mPEG) and bis-OH polyethylene glycols are preferred.

Activation of Polymers

If the polymeric molecules to be conjugated with the polypeptide in question are not active it must be activated by the use of a suitable technique. It is also contemplated according to the invention to couple the polymeric molecules to the polypeptide through a linker. Suitable linkers are well-known to the skilled person.

Methods and chemistry for activation of polymeric molecules as well as for conjugation of polypeptides are intensively described in the literature. Commonly used methods for activation of insoluble polymers include activation of functional groups with cyanogen bromide, periodate, glutaraldehyde, biepoxides, epichlorohydrin, divinylsulfone, carbodiimide, sulfonyl halides, trichlorotriazine etc. (see R. F. Taylor, (1991), "Protein immobilisation. Fundamental and applications", Marcel Dekker, N.Y.; S. S. Wong, (1992), "Chemistry of Protein Conjugation and Crosslinking", CRC Press, Boca Raton; G. T. Hermanson et al., (1993), "Immobilized Affinity Ligand Techniques", Academic Press, N.Y.). Some of the methods concern activation of insoluble polymers but are also applicable to activation of soluble polymers e.g. periodate, trichlorotriazine, sulfonylhalides, divinylsulfone, carbodiimide etc. The functional groups being amino, hydroxyl, thiol, carboxyl, aldehyde or sulfydryl on the polymer and the chosen attachment group on the protein must be considered in choosing the activation and conjugation chemistry which normally consist of i) activation of polymer, ii) conjugation, and iii) blocking of residual active groups.

In the following a number of suitable polymer activation methods will be described shortly. However, it is to be understood that also other methods may be used.

Coupling polymeric molecules to the free acid groups of polypeptides may be performed with the aid of diimide and for example amino-PEG or hydrazino-PEG (Pollak et al., (1976), J. Amr. Chem. Soc., 98, 289–291) or diazoacetate/amide (Wong et al., (1992), "Chemistry of Protein Conjugation and Crosslinking", CRC Press).

Coupling polymeric molecules to hydroxy groups is generally very difficult as it must be performed in water. Usually hydrolysis predominates over reaction with hydroxyl groups.

Coupling polymeric molecules to free sulfhydryl groups can be reached with special groups like maleimido or the ortho-pyridyl disulfide. Also vinylsulfone (U.S. Pat. No. 5,414,135, (1995), Snow et al.) has a preference for sulfhydryl groups but is not as selective as the other mentioned.

Accessible Arginine residues in the polypeptide chain may be targeted by groups comprising two vicinal carbonyl groups.

Techniques involving coupling electrophilically activated PEGs to the amino groups of Lysines may also be useful. Many of the usual leaving groups for alcohols give rise to an amine linkage. For instance, alkyl sulfonates, such as tresylates (Nilsson et al., (1984), Methods in Enzymology vol. 104, Jacoby, W. B., Ed., Academic Press: Orlando, p. 56–66; Nilsson et al., (1987), Methods in Enzymology vol. 135; Mosbach, K., Ed.; Academic Press: Orlando, pp. 65–79; Scouten et al., (1987), Methods in Enzymology vol. 135, Mosbach, K., Ed., Academic Press: Orlando, 1987; pp 79–84; Crossland et al., (1971), J. Amr. Chem. Soc. 1971, 93, pp. 4217–4219), mesylates (Harris, (1985), supra; Harris et al., (1984), J. Polym. Sci. Polym. Chem. Ed. 22, pp 341–352), aryl sulfonates like tosylates, and para-nitrobenzene sulfonates can be used.

Organic sulfonyl chlorides, e.g. Tresyl chloride, effectively converts hydroxy groups in a number of polymers, e.g. PEG, into good leaving groups (sulfonates) that, when reacted with nucleophiles like amino groups in polypeptides allow stable linkages to be formed between polymer and polypeptide. In addition to high conjugation yields, the reaction conditions are in general mild (neutral or slightly alkaline pH, to avoid denaturation and little or no disruption of activity), and satisfy the non-destructive requirements to the polypeptide.

Tosylate is more reactive than the mesylate but also more unstable decomposing into PEG, dioxane, and sulfonic acid (Zalipsky, (1995), Bioconjugate Chem., 6, 150–165). Epoxides may also been used for creating amine bonds but are much less reactive than the above mentioned groups.

Converting PEG into a chloroformate with phosgene gives rise to carbamate linkages to Lysines. This theme can be played in many variants substituting the chlorine with N-hydroxy succinimide (U.S. Pat. No. 5,122,614, (1992); Zalipsky et al., (1992), Biotechnol. Appl. Biochem., 15, p. 100–114; Monfardini et al., (1995), Bioconjugate Chem., 6, 62–69, with imidazole (Allen et al., (1991), Carbohydr. Res., 213, pp 309–319), with para-nitrophenol, DMAP (EP 632 082 A1, (1993), Looze, Y.) etc. The derivatives are usually made by reacting the chloroformate with the desired leaving group. All these groups give rise to carbamate linkages to the peptide.

Furthermore, isocyanates and isothiocyanates may be employed yielding ureas and thioureas, respectively.

Amides may be obtained from PEG acids using the same leaving groups as mentioned above and cyclic imide thrones (U.S. Pat. No. 5,349,001, (1994), Greenwald et al.). The reactivity of these compounds is very high but may make the hydrolysis too fast.

PEG succinate made from reaction with succinic anhydride can also be used. The hereby comprised ester group make the conjugate much more susceptible to hydrolysis (U.S. Pat. No. 5,122,614, (1992), Zalipsky). This group may be activated with N-hydroy succinimide.

Furthermore, a special linker can be introduced. The oldest being cyanuric chloride (Abuchowski et al., (1977), J. Biol. Chem., 252, 3578–3581; U.S. Pat. No. 4,179,337, (1979), Davis et al.; Shafer et al., (1986), J. Polym. Sci. Polym. Chem. Ed., 24, 375–378.

Coupling of PEG to an aromatic amine followed by diazotation yields a very reactive diazonium salt which in situ can be reacted with a peptide. An amide linkage may also be obtained by reacting an azlactone derivative of PEG (U.S. Pat. No. 5,321,095, (1994), Greenwald, R. B.) thus introducing an additional amide linkage.

As some peptides do not comprise many Lysines it may be advantageous to attach more than one PEG to the same Lysine. This can be done e.g. by the use of 1,3-diamino-2-propanol.

PEGs may also be attached to the amino-groups of the enzyme with carbamate linkages (WO 95/11924, Greenwald et al.). Lysine residues may also be used as the backbone.

Position of the Coupled Polymeric Molecules

Virtually all ionized groups, such as the amino group of Lysine residues, are on the surface of the polypeptide molecule (see for instance Thomas E. Creighton, (1993), "Proteins", W. H. Freeman and Company, New York). Therefore, the number of readily accessible attachment groups (i.e. amino groups) on the polypeptide's surface equals the number of Lysine residues in the primary structure of the polypeptide plus the N-terminus amino group.

According to the invention from 1 to 100 polymeric molecules, preferably 4 to 50 polymeric molecules, 5 to 35 polymeric molecules are coupled to the parent polypeptide.

The Parent Polypeptide

The modified polypeptides of the invention may be prepared on the basis of parent polypeptides, typically having a molecular weight in the range from 5 to 100 kDa, preferably from 15 to 60 kDa, using any suitable technique known in the art.

The term "parent" polypeptide is intended to indicate any uncoupled polypeptide (i.e. a polypeptide to be modified).

The polypeptide may preferably be of microbial origin, such as bacterial, filamentous fungus or yeast origin. The parent polypeptide may be a naturally-occurring (or wild-type) polypeptide or may be a variant thereof.

Preferred polypeptides are enzymes and polypeptides with anti-microbial activity. In a preferred embodiment the enzyme is an enzyme suitable for skin care compositions and products having a substantially enzymatic activity in the pH range used in the skin care product.

When choosing a parent polypeptide it is advantageous to use a polypeptide with a high number of attachment groups.

Further, in a preferred embodiment of the invention the polymeric molecules are spread broadly over the surface of the polypeptide. For enzymes it is preferred that no polymeric molecules are coupled in the area close to the active site.

In the present context "spread broadly" means positioned so that the polymeric molecules coupled to the attachment groups of the polypeptide shields different parts of the polypeptide surface, preferably the whole or close to the whole surface area to make sure that the relevant epitope(s) being recognisable are shielded and hereby not recognised by the immune system's antibodies. It is believed that the surface area of interaction between the polypeptide and an antibody lies in the range about 500 Å$^2$ (26×19 Å) (see Sheriff et al. (1987), Proc. Natl. Acad. Sci. USA, Vol. 84, p. 8075).

Two or more attachment groups on the polypeptide should preferably not lie close to each other as it will probably result in only one polymeric molecule being coupled.

For enzyme it is preferred, to ensure a minimal loss of enzymatic activity, not to couple polymeric molecules in a close distance of the active site. Generally seen it is preferred that no polymeric molecules are attached within 5 Å, preferred 10 Å from the active site.

Further, polypeptides having coupled polymeric molecules at known epitope recognisable by the immune system or close to said epitope are also considered advantageous according to the invention. If the position of the epitope(s) is (are) unknown it is advantageous to couple as many polymeric molecules to the attachment groups available on the surface of the polypeptide. It is preferred that said attachment groups are spread broadly over the surface of the polypeptide in a suitable distance from the active site.

Modified polypeptides fulfilling the above claims to the distribution of coupled polymeric molecules on the surface of the polypeptide are preferred according to the invention.

For enzymes especially enzymes having no or only very few polymeric molecules (i.e. 0 to 2) coupled within a distance of 0 to 5 Å, preferably 0 to 10 Å from the active site are preferred.

The Enzyme Activity

The parent enzyme may have any activity known to be used for skin care. Contemplated enzymes including Oxidoreductases (E.C. 1, "Enzyme Nomenclature, (1992), Academic Press, Inc.), such as laccase and Superoxide dismutase (SOD); Hydrolases E.C. 3, including proteases, especially serine proteases such as subtilisins, and lipolytic enzymes; Transferases, (E.C. 2), such as transglutaminases (TGases); Isomerases (E.C. 5), such as Protein disulfide Isomerases (PDI).

Hydrolases

Proteolytic Enzymes

Contemplated proteolytic enzymes include proteases selected from the group of acidic aspartic proteases, cysteine proteases, serine proteases, such as subtilisins, or metalloprotease, with the above indicated properties (i.e. number of attachment groups, position of attachment groups etc.).

Specific examples of suitable parent proteases having a suitable number of attachment groups are indicated in Table 1 below:

TABLE 1

| Enzyme | Number of attachment groups | Molecular weight kDa | Reference |
| --- | --- | --- | --- |
| PD498 | 13 | 29 | Seq. ID No. 2 WO 93/24623 |
| SAVINASE ® | 6 | 27 | von der Osten et al., (1993), Journal of Biotechnology, 28, p. 55+ |
| Proteinase K | 9 | 29 | Gunkel et al., (1989), Eur. J. Biochem, 179, p. 185–194 |
| Proteinase R | 5 | 29 | Samal et al., (1990), Mol. Microbiol, 4, p. 1789–1792 |
| Proteinase T | 14 | 29 | Samal et al., (1989) Gene, 85, p. 329–333 |
| Subtilisin DY | 13 | 27 | Betzel et al. (1993), Arch. Biophys, 302, no. 2, p. 499–502 |
| Lion Y | 15 | 46 | SEQ. ID NO. 4 JP 04197182-A |
| RENNILASE ® |  | 39 | Available from Novo Nordisk A/S |
| Ja16 | 5 | 28 | WO 92717576 |
| Thermolysin | 12 | 34 | Titani et al., (1972) Nature New Biol. 238, p. 35–37, and SEQ ID NO 5 |
| ALCALASE ® (a natural) subtilisin Carlsberg variant) | 10 | 27 | von der Osten et al., (1993), Journal of Biotechnology, 28, p. 55+ |

The subtilisin PD498 has a molecular weight of 29 kDa, and as can be seen from SEQ ID NO: 2, 12 Lysine groups for polymer attachment on the surface of the enzyme plus one N-terminal amino group. As mentioned above preferred enzymes have Lysines spread broadly over the surface. PD498 has no Lysine residues in a distance of 0–10 Å from the active site which makes it especially suitable in modified form. Further, the Lysine residues are spread broadly on the surface of the enzyme (i.e. away from the active site).

The enzyme Subtilisin DY has a molecular weight of 27 kDa and has 12 amino groups (i.e. Lysine residues) on the surface of the enzyme and one N-terminal amino group (see SEQ ID NO: 3).

The parent protease Lion Y has a molecular weight of 46 kDa and has 14 amino groups (i.e. Lysine residues) on the surface of the enzyme plus one N-terminal amino group (see SEQ ID NO: 4).

The neutral metalloprotease Thermolysin has a molecular weight of about 34 kDa and has 11 amino groups (i.e. Lysine residues) on the surface plus one N-terminal amino group. (See SEQ ID NO: 5).

Lipolytic Enzymes

Contemplated lipolytic enzymes include *Humicola lanuginosa* lipases, e.g. the one described in EP 258 068 and EP 305 216, *Humicola insolens*, a *Rhizomucor miehei* lipase, e.g. as described in EP 238 023, *Absidia* sp. lipolytic enzymes (WO 96/13578), a *Candida* lipase, such as a *C. antarctica* lipase, e.g. the *C. Antarctica* lipase A or B described in EP 214 761, a Pseudomonas lipase such as a *P. alcaligenes* and *P. pseudoalcaligenes* lipase, e.g. as described in EP 218 272, a *P. cepacia* lipase, e.g. as described in EP 331 376, a Pseudomonas sp. lipase as disclosed in WO 95/14783, a Bacillus lipase, e.g. a *B.*

*subtilis* lipase (Dartois et al., (1993) Biochemica et Biophysica acta 1131, 253–260), a *B. stearothermophilus* lipase (JP 64/744992) and a *B. Pumilus* lipase (WO 91/16422). Other types of lipolytic include cutinases, e.g. derived from *Humicola insolens* or *Pseudomonas mendocina* (WO 88/09367), or a cutinase derived from *Fusarium solani pisi* (WO 90/09446).

Oxidoreductases

Laccases

Contemplated laccases include the laccases disclosed in WO 96/00290 and WO 95/33836 from Novo Nordisk.
Other oxidoreductases include catalase, glucose oxidase, peroxidase, superoxide dismutase and lipoxygenase.

Transferases

Transglutaminases

Suitable transferases include any transglutaminases disclosed in WO 96/06931 (Novo Nordisk A/S) and WO 96/22366 (Novo Nordisk A/S).

Isomerases

Protein Disulfide Isomerase

Without being limited thereto suitable protein disulfide isomerases include PDIs described in WO 95/01425 (Novo Nordisk A/S).

Industrial Composition

In a further aspect the invention relates to an "industrial composition" comprising a modified polypeptide with reduced allergenicity.

In the context of the present invention an "industrial composition" means a composition which is not intended to be introduced into the circulatory system. In other words it means a composition which is not intended for intradermally, intravenously or subcutaneously administration.

As mentioned above the main problem for polypeptides, such as enzymes, for industrial application is the potential risk of respiratory allergy caused by inhalation through the respiratory system i.e. intratracheally or intranasal exposure.

Examples of "industrial composition" are polypeptides, especially enzymes and anti-microbial polypeptides, used in compositions or products such as detergents, including laundry and dish washing detergents, household article products, agro-chemicals, personal care products, such as skin care products, including cosmetics and toiletries, oral and dermal pharmaceuticals, compositions used for treating/processing textiles, compositiorns for hard surface cleaning, and compositions used for manufacturing food and feed, including food or feed additives, such as additives for making bread or the like etc. Especially contemplated according to the invention are skin care products and detergents.

Skin Care Products

In the context of the present invention 'skin care products" cover all personal care products used for cleansing, care and/or beautification of the skin of the body and further other products, such as hair care products, which during use may come in contact with the skin or respiratory system. Also corresponding products for animals are contemplated according to the present invention.

Specific examples of skin care products contemplated according to the present invention are soap, cosmetics, skin creams, skin gels, skin milk, skin lotion, cleansing cream, cleansing lotion, cleansing milk, cold cream, cream soap, makeup base, milky lotion, pack, calamine lotion, T zone essence, hand cream, essence powder, whitening powder, powder soap, cake soap, transparent soap, lip cream, lipstick, nourishing essence, creamy foundation, face powder, powder eye-shadow, powder foundation, nail polish remover, hair tonic, hair liquid, hair cream, hair gel, hair treatment, hair setting preparations, hair dyes, hair colorants, scalp treatment, shampoo, balsam, hair rinse, hair spray sun oil, sun screen, shaving foam and gel, shaving cream, baby oil, acne care products, antiperspirants, insect repellents, deodorants etc.

Enzyme Activities Suitable for Skin Care

Skin care compositions of the invention comprise modified enzymes with reduced allergenicity and ingredients known to be used in skin care compositions A number of enzyme activities are known to be used skin care compositions.

Proteases

Proteases are effective ingredients in skin cleaning products. Proteases remove the upper layer of dead keratinous skin cells and thereby makes the skin look brighter and more fresh. Further, proteases also improve the smoothness of the skin.

Proteases are used in toiletries, bath and shower products, including shampoos, conditioners, lotions, creams, soap bars, toilet soaps, and liquid soaps.

Lipases

Lipases can be applied for cosmetic use as active ingredients in skin cleaning products and anti-acne products for removal of excessive skin lipids, and in bath and shower products such as creams and lotions as active ingredients for skin care.

Lipases can also be used in hair cleaning products (e.g. shampoos) for effective removal of sebum and other fatty material from the surface of hair.

Oxidoreductases

The most common oxidoreductase for personal care purposes is an oxidase (usually glucose oxidase) with substrate (e.g. glucose) that ensures production of $H_2O_2$, which then will initiate the oxidation of for instance $SCN^-$ or $I^-$ into anti-microbial reagents ($SCNO^-$ or $I_2$) by a peroxidase (usually lactoperoxidase). This enzymatic complex is known in nature from e.g. milk and saliva.

It is being utilised commercially as anti-microbial system in oral care products (mouth rinse, dentifrice, chewing gum), where it also can be combined with an amyloglucosidase to produce the glucose. These systems are also known in cosmetic products for preservation.

Another application of oxidoreductases is oxidative hair dyeing using oxidases, peroxidases and laccases (See e.g. WO 96/00290 or WO 95/33836 from Novo Nordisk).

Free radicals formed on the surface of the skin (and hair) known to be associated with the ageing process of the skin (spoilage of the hair).

The free radicals activate chain reactions that leads to destruction of fatty membranes, collagen, and cells.

The application of free radical scavengers such as Superoxide dismutase into cosmetics is well-known (R. L. Goldemberg, DCI, November 93, p. 48–52).

Protein disulfide isomerase (PDI) is also an oxidoreductase. It may be utilised for waving of hair (reduction and reoxidation of disulfide bonds in hair) and repair of spoiled hair (where the damage is mainly reduction of existing disulfide bonds).

Transglutaminase

Skin care compositions for application to human skin, hair or nails comprise (a) an amino-functional active ingredient, (b) transglutaminase to catalyse cross-linking of the active ingredient to the skin, hair or nails, and (c) a carrier is known from U.S. Pat. No. 5,490,980.

A cosmetic composition suitable for application to mammalian skin, hair or nails comprising: (a) at least one corneocyte envelope protein in an amount sufficient to provide a protective layer on said skin, hair or nails; (b) a transglutaminase in an amount sufficient to form covalent bonds between the corneocyte envelope protein and externally exposed corneocyte proteins present in the stratum corneum of said skin, hair or nails; (c) calcium ions in an amount sufficient to activate the transglutaminase; and (d) a cosmetically acceptable vehicle, wherein the composition comprises an emulsion having two phases and wherein the corneocyte envelope protein is contained in one of the phases and the transglutaminase is contained within the other phase (see U.S. Pat. No. 5,525,336).

JP 3083908 describes a skin cosmetic material contains a transglutaminase modified with a water-soluble substance. The modifying substance is, e.g., one or more of polyethylene glycol, ethylene glycol, propylene glycol, glycerine, polyvinyl alcohol, glucose, sucrose, alginil acid, carboxymethyl cellulose, starch, and hydroxypropyl cellulose. The modification is done, e.g., by introducing reactive groups and bonding to the enzyme. For providing a material mild to the skin, causing less time-lapse discolouring and odorising, and having good effects of curing rough skin, retaining moisture, and conditioning the skin beautifully.

The Skin Care Products of the Invention

In the third aspect the invention relates to a skin care product comprising a skin care composition of the invention. The term "skin care products" are defined above.

A skin care product of the invention may comprise from an effective amount of modified enzymes of the invention. Such effective amounts known to the skilled person may will often lie in the range from above 0 to 5% of the final skin care product.

Contemplated skin care products of the invention include, without being limited thereto, the following products: soap, cosmetics, skin creams, skin milk, skin lotion, skin gel, cleansing cream, cleansing lotion, cleansing milk, cold cream, cream soap, makeup base, milky lotion, pack, calamine lotion, T zone essence, hand cream, essence powder, whitening powder, powder soap, cake soap, transparent soap, lip cream, lipstick, nourishing essence, creamy foundation, face powder, powder eye-shadow, powder foundation, nail polish remover, hair tonic, hair liquid, hair cream, hair gel, hair treatment, hair setting preparations, hair dyes, hair colorants, scalp treatment, shampoo, balsam, hair rinse, hair spray sun oil, sun screen, shaving foam, shaving cream, baby oil, acne care products, antiperspirants, insect repellents, deodorants etc.

General Skin Care Product Formulations

The term "ingredients used in skin care products" is meant to cover all ingredients which are known to be used in skin care product formulations. Examples of such ingredients can be found in "Cosmetics and Toiletries" edited by Wilfried Umbach and published by Ellis Horwood, Limited, England, (1991), and "Surfactants in Consumer Products", edited by J. Falbe and published by Spring-Verlag, (1987).

In the following a non exhausting list of guide formulations are listed. These provide an overview of formulations of important skin care products contemplated according to the invention.

Toilet soap

| Ingredients | Examples | % |
|---|---|---|
| Surfactants | Soap (sodium salt) | 83–87 |
| Sequestering agents | Ethylenediamine tetraacetate | 0.1–0.3 |
| Consistency regulators | Sodium chloride | approx. 0.5 |
| Dyestuffs | | <0.1 |
| Optical brighteners | | <0.1 |
| Antioxidants | 2,6-bis(1,1-Dimethylethyl)-4-methyl phenol (BHT) | 0.1–0.3 |
| Whitening agents | Titanium dioxide | 0.1–0.3 |
| Fragrances | | 1.0–2.0 |
| Enzymes | Protease/Lipase | 0–5 |
| Water | Balance | |

Syndet (Synthetic Detergents)

| Ingredients | Examples | % |
|---|---|---|
| Surfactants | Lauryl sulfate | 30–50 |
| | Lauryl sulfo succinate | 1–12 |
| Refatting agents | Fatty alcohols | 10–20 |
| Plasticizers | Stearyl mono/diglycerides | 0–10 |
| Fillers | Starches | 0–10 |
| Active agents | Salicylic acid | 0–1 |
| Dyestuffs | | <0.2 |
| Fragrances | | 0–2 |
| Enzymes | Protease/Lipase | 0–5 |
| Water | Balance | |

Foam bath and shower bath

| Ingredients | Examples | % | % |
|---|---|---|---|
| | | Foam bath | Shower bath |
| Surfactants | Lauryl ether sulfate | 10–20 | 10–12 |
| | Coco amidopropyl dimethyl betaine | 2–4 | 2–4 |
| | Ethoxylated fatty acids | 0.5–2 | — |
| Refatting agents | Fatty alcohols | 0.5–3 | |
| | Ethoxylated fatty alcoho. | 0.5–5 | 0–4 |
| Enzymes | Protease/Lipase | 0–5 | 0–5 |

| Ingredients | Examples | % | % |
|---|---|---|---|
| | | Foam bath | Shower bath |
| Foam stabilizers | Fatty acid alkanol amide | 0.2–2 | 0–4 |
| Conditioners | Quaternized hydroxypropyl cellulose | — | 0–0.5 |
| Thickeners | Sodium chloride | 0–3 | 0–3 |
| Pearlescent agents | Ethylene glycol stearate | 0–2 | — |
| Active agents | Vegetable extracts | 0–1 | 0–1 |
| Preservatives | 5-Bromo-5-nitro-1,3-dioxane | 0.1 | 0.1 |
| Dyestuffs | | 0.1–0.2 | 0.1 |
| Fragrances | | 0.3–3 | 0.3–2 |
| Enzymes | Protease/Lipase | 0–5 | 0–5 |
| Water | Balance | Balance | Balance |

Skin cream (water-in-oil type and oil-in-water type)

| Ingredients | Examples | % | |
|---|---|---|---|
| | | Water-in-oil/ type | Oil-in-water type |
| Emulsifiers | Sorbitane sesquioleate | 3–5 | — |
| | Aluminum stearate | 1–2 | — |
| | Triethanolamine stearate | — | 1–2 |
| | Cetyl/Stearyl alcohol polyglycol ethers | — | 1–3 |
| Fatty derivatives | Isopropyl palmitate | 1–5 | 0–3 |
| | Cetyl/Stearyl alcohol | — | 0–2 |
| | 2-Octyl dodecanol | 2–10 | 3–7 |
| | Stearic/Palmitic acid | — | 0–3 |
| | Caprylic/Capric acid triglycerides | 5–10 | — |
| | Glycerine stearate | — | 0–5 |
| Moisturizers | Glycerine | 1–5 | 1–5 |
| | Sorbitol | 1–5 | 1–5 |
| | Poly (hydroxy carboxylic acids) | 0.5–2 | — |

-continued

| | | % | % |
|---|---|---|---|
| Stabilizers | Propyleneglycol | — | 0–3 |
| | Magnesium sulfate | 0–0.8 | — |
| Preservatives | p-Hydroxy benzoic acid ester | 0.2–0.4 | 0.2–0.4 |
| Enzymes | Protease/Lipase | 0–5 | 0–5 |
| Water | Balance | Balance | |

Body lotion (oil-in-water type) and skin lotion for application on the wet skin

| Ingredients | Examples | % | % |
|---|---|---|---|
| | | Body lotion | Skin lotion |
| Emulsifiers polyglycol ethers | Cetyl/Stearyl alcohol | 1–3 | — |
| Sorbitane monolaurate | | 0.5–1 | — |
| Sodium stearate | | — | 1–2 |
| Sodium lauryl ether sulfate | — | 0.5–2 | |
| Fatty derivatives | 2-Octyl dodecanol | 1–3 | 0–5 |
| Paraflin oils | | — | 20–25 |
| Bees wax | | 0.5–1 | — |
| Isooctyl stearate | | 3–7 | — |
| Isopropyl palmitate | | — | 2–5 |
| Moisturizers | Glycerine | 3–5 | 5–10 |
| Sorbitol | — | 0–5 | |
| Thickeners | Polyacrylates | 0–0.3 | 0–1 |
| | Methyl hydroxypropyl cellulose | 0–0.3 | 0–0.5 |
| Preservatives | p-Hydroxy benzoic acid ester | 0.2–0.4 | 0.2–0.4 |
| Enzymes | Protease/Lipase | 0–5 | 0–5 |
| Water | Balance | Balance | |

Face lotion

| Ingredients | Examples | % |
|---|---|---|
| Surfactants | Magnesium lauryl ether sulfate | 0.2–0.5 |
| Refatting agents | Di-n-butyl adipate | 1–2 |
| Solubilizers | Castor oil polyglycol ethers | 0.1–1 |
| Cleaning and refreshing components | Ethanol | 0–15 |
| Moisturizers | Glycerine | 0–5 |
| | Sorbitol | 0–5 |
| Preservatives | p-Hydroxy benzoic acid ester | 0.2–0.4 |
| Adstringents | Vegetable extracts | 1–5 |
| Antiirritants | Panthenol | 0–1 |
| | Allantoine | 0–0.2 |
| | Vegetable extracts | 0.5–3 |
| Enzymes | Protease/Lipase | 0–5 |
| Water | Balance | |

Hair shampoo

| Ingredients | Examples | % |
|---|---|---|
| Surfactants | Lauryl ether sulfate | 12–16 |
| | Coco fatty acid amidopropyl dimethyl betaine | 2–5 |
| | Fatty acid polyglycol esters | 0–2 |
| Foam boosters | Fatty acid ethanol amides | 0.5–2.5 |
| Conditioners | Quaternized hydroxyethyl cellulose | 0.4–1 |
| Protein hydrolysates | | 0.2–1 |
| Refatting agents | Ethoxylated lanolin alcohols | 0.2–1 |
| Additives | Anti-dandruff agents | 0–1 |
| Preservatives | 5-Bromo-5-nitro-1,3-dioxane | 0.1–0.3 |
| Pearlescent agents | Ethyleneglycol stearate | 0–2 |
| Dyestuffs | | <0.1 |
| pH-Regulators | Acids/Bases | 0.1–1 |
| Fragrances | | 0.3–0.5 |
| Enzymes | Protease/Lipase | 0–5 |
| Water | Balance | |

-continued

Hair rinse and hair conditioner

| Ingredients | Examples | % | % |
|---|---|---|---|
| | | Hair rinse | Hair conditioner |
| Surfactants | Fatty alcohol polyglycol ethers | 0.1–0.2 | 1.5–2.5 |
| | Cetyl trimethyl ammonium chloride | 0.5–1 | — |
| | Dimethyl benzyl stearyl ammonium chloride | — | 0.5–1 |
| Refatting agents | Cetyl/Stearyl mono/diglyceride | 0.5–1.5 | 1.5–2.5 |
| Consistency regulators | Fatty alcohols | 1–2.5 | 2.5–3.5 |
| Thickeners | Methyl hydroxypropyl cellulose | 0.3–0.6 | 0.4–0.8 |
| Conditioners | Quaternized hydroxyethyl cellulose | 0.1–0.3 | 0.3–0.4 |
| Preservatives | p-Hydroxy benzoic acid ester | 0.1–0.3 | 0.1–0.3 |
| Dyestuffs | | <0.1 | <0.1 |
| pH-Regulators | Acids/Bases | 0.1–1 | 0.1–1 |
| Fragrances | | 0.2–0.5 | 0.2–0.5 |
| Enzymes | Protease/Lipase | 0–5 | 0–5 |
| Water | Balance | Balance | |

Hair dyes

| Ingredients | Examples | % |
|---|---|---|
| Component 1: | Alkaline dyeing cream | |
| Surfactants | Lauryl ether sulfate | 1–4 |
| | Ethoxylated castor oil | 1–2 |
| Consistency regulators | Fatty alcohols | 8–10 |
| Reductants | Sodium sulfite | 0.8–1.2 |
| Buffers | Ammonium chloride | 0.5–1 |
| Sequestrants | 1-Hydroxyethane-1,1-diphosphonic acid | 0.1–0.2 |
| Alkaline agents | Ammonia | 1.2–2 |
| Oxidation dyestuffs | Developing agents | 1 |
| Coupling agents | | 1 |
| Enzyme | Laccase | 0–5 |
| Water | Balance | |
| Component II: | Hydrogen peroxide dispersion | |
| Surfactants | Lauryl ether sulfate | 0.5–1 |
| Oxidants | Hydrogen peroxide | 6–9 |
| Stabilizers | 1-Hydroxyethane-1,1-diphosphonic acid | 1–1.5 |
| Thickeners | Polyacrylates | 3–5 |
| Enzyme | Laccase | 0–5 |
| Water | Balance | |

Shaving cream

| Ingredients | Examples | % |
|---|---|---|
| Soaps | Palmitic/Stearic acid | 30–40 |
| | Potassium hydroxide | 5–7 |
| | Sodium hydroxide | 1–2 |
| Fatty components | Coconut oil | 5–10 |
| | Polyethyleneglycol | 0–2 |
| Stabilizers | Sodium tetraborate | 0–0.5 |
| | Sodium silicate | 0–0.5 |
| | Sorbitol | 0–3 |
| Enzyme | Protease | 0–5 |
| Water | Balance | |

Shaving lotion

| Ingredients | Examples | % |
|---|---|---|
| Disinfecting and phonic acid | Ethanol | 40–80 |

| | -continued | |
|---|---|---|
| Refatting agents | Di-n-butyl adipate | 1–2 |
| Solubilizers | Ethoxylated castor oil | 0.5–1 |
| Adstringents | Vegetable extracts | 1–10 |
| Antiirritants | Panthenol | 0–0.5 |
| Vegetable extracts | | 0–2 |
| Stabilizers | Glycerine | 0–5 |
| | Sorbitol | 0–5 |
| | Propyleneglycol | 0–3 |
| Enzymes | Protease | 0–5 |
| Water | | Balance |

Hair pomade

| Ingredients | Examples | % |
|---|---|---|
| Consistency regulators | Fatty alcohols | 4–5 |
| | Ethoxylated lanolin alcohols | 3–6 |
| Mineral fats | Vaseline | 45–52 |
| | Branched chain paraffins | 10–18 |
| Antioxidants | 2,6-bis(1,1-Dimethylethyl)-4-methyl phenol (BHT) | 0.5–1 |
| Fragrances | | 0.2–0.4 |
| Dyestuffs | | 0.1 |
| Enzymes | Lipase | 0–5 |
| Emollients | Glycerine | Balance |

Setting lotion

| Ingredients | Examples | % |
|---|---|---|
| Solvents | Isopropanol | 12–20 |
| Film forming components | Vinyl pyrrolidone/vinyl acetate copolymers | 2–3.5 |
| Softening agents | Vinyl pyrrolidone/dimethyl amino ethyl methacrylate | 0.2–1 |
| Conditioners | Protein hydrolysates | 0.2–0.5 |
| Antistatics | Cetyl trimethyl ammonium chloride | 0.1–0.5 |
| Emulsifiers | Ethoxylated castor oil | 0.1–0.5 |
| Fragrances | | 0.1–0.2 |
| Dyestuffs | | <0.1 |
| Enzymes | Lipase | 0–5 |
| Water | | Balance |

In a further aspect the invention relates to the use of modified polypeptide of the invention for reducing the allergenicity of industrial compositions and products as defined above.

In a final aspect the invention relates to a method for reducing the respiratory allergenicity of polypeptides comprising the step of coupling.

Detergent Disclosure

The detergent compositions of the invention may for example, be formulated as hand and machine laundry detergent compositions including laundry additive compositions and compositions suitable for use in the pretreatment of stained fabrics, rinse added fabric softener compositions, and compositions for use in general household hard surface cleaning operations and dishwashing operations.

The detergent composition of the invention comprises the conjugate of the invention and a surfactant. Additionally, it may optionally comprise a builder, another enzyme, a suds suppresser, a softening agent, a dye-transfer inhibiting agent and other components conventionally used in detergents such as soil-suspending agents, soil-releasing agents, optical brighteners, abrasives, bactericides, tarnish inhibitors, coloring agents, and/or encapsulated or nonencapsulated perfumes.

The detergent composition according to the invention can be in liquid, paste, gels, bars or granular forms. The pH (measured in aqueous solution at use concentration) will usually be neutral or alkaline, e.g. in the range of 7–11.

Granular compositions according to the present invention can also be in "compact form", i.e. they may have a relatively higher density than conventional granular detergents, i.e. form 550 to 950 g/l. The enzyme conjugate of the invention, or optionally another enzyme incorporated in the detergent composition, is normally incorporated in the detergent composition at a level from 0.00001% to 2% of enzyme protein by weight of the composition, preferably at a level from 0.0001% to 1% of enzyme protein by weight of the composition, more preferably at a level from 0.001% to 0.5% of enzyme protein by weight of the composition, even more preferably at a level from 0.01% to 0.2% of enzyme protein by weight of the composition.

Surfactant System

The surfactant system may comprise nonionic, anionic, cationic, ampholytic, and/or zwitterionic surfactants. The surfactant system preferably consists of anionic surfactant or a combination of anionic and nonionic surfactant, e.g. 50–100% of anionic surfactant and 0–50% nonionic. The laundry detergent compositions may also contain cationic, ampholytic, zwitterionic, and semi-polar surfactants, as well as the nonionic and/or anionic surfactants other than those already described herein. The surfactant is typically present at a level from 0.1% to 60% by weight. Some examples of surfactants are described below.

Nonionic Surfactant

The surfactant may comprise polyalkylene oxide (e.g. polyethylene oxide) condensates of alkyl phenols. The alkyl group may contain from about 6 to about 14 carbon atoms, in a straight chain or branched-chain. The ethylene oxide may be present in an amount equal to from about 2 to about 25 moles per mole of alkyl phenol.

The surfactant may also comprise condensation products of primary and secondary aliphatic alcohols with about 1 to about 25 moles of ethylene oxide. The alkyl chain of the aliphatic alcohol can either be straight or branched, and generally contains from about 8 to about 22 carbon atoms.

Further, the nonionic surfactant may comprise polyethylene oxide condensates of alkyl phenols, condensation products of primary and secondary aliphatic alcohols with from about 1 to about 25 moles of ethylene oxide, alkylpolysaccharides, and mixtures hereof. Most preferred are C8–C14 alkyl phenol ethoxylates having from 3 to 15 ethoxy groups and C8–C18 alcohol ethoxylates (preferably C10 avg.) having from 2 to 10 ethoxy groups, and mixtures thereof.

Anionic Surfactants

Suitable anionic surfactants include alkyl alkoxylated sulfates which are water soluble salts or acids of the formula RO(A)mSO3M wherein R is an unsubstituted C10–C-24 alkyl or hydroxyalkyl group having a C10–C24 alkyl component, preferably a C12–C20 alkyl or hydroxyalkyl, more preferably C12–C18 alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl, trimethyl-ammonium cations and quaternary ammonium cations such as tetramethyl-ammonium and dimethyl piperdinium cations and those derived from alkylamines such as ethylamine, diethylamine, triethylamine, mixtures thereof, and the like.

Other suitable anionic surfactants include the alkyl sulfate surfactants which are water soluble salts or acids of the formula ROSO3M wherein R preferably is a C10–C24 hydrocarbyl, preferably an alkyl or hydroxyalkyl having a C10–C20 alkyl component, more preferably a C12–C18 alkyl or hydroxyalkyl, and M is H or a cation, e.g., an alkali metal cation (e.g. sodium, potassium, lithium), or ammonium or substituted ammonium.

Other anionic surfactants include salts (including, for example, sodium, potassium, ammonium, and substituted ammonium salts such as mono- di- and triethanolemine salts) of soap, C8–C22 primary or secondary alkanesulfonates, C8–C24 olefinsulfonates, sulfonated polycarboxylic acids prepared by sulfonation of the pyrolyzed product of alkaline earth metal citrates. Alkylbenzene sulfonates are suitable, especially linear (straight-chain) alkyl benzene sulfonates (LAS) wherein the alkyl group preferably contains from 10 to 18 carbon atoms.

The laundry detergent compositions typically comprise from about 1% to about 40%, preferably from about 3% to about 20% by weight of such anionic surfactants.

Builder System

The compositions according to the present invention may further comprise a builder system. Any conventional builder system is suitable for use herein including aluminosilicate materials, silicates, polycarboxylates and fatty acids, materials such as ethylenediamine tetraacetate (EDTA), metal ion sequestrants such as aminopolyphosphonates. Phosphate builders can also be used herein.

Suitable builders can be an inorganic ion exchange material, commonly an inorganic hydrated aluminosilicate material, more particularly a hydrated synthetic zeolite such as hydrated zeolite A, X, B, HS or MAP.

Detergency builder salts are normally included in amounts of from 5% to 80% by weight of the composition. Preferred levels of builder for liquid detergents are from 5% to 30%.

Other Detergent Enzyme Activities

The detergent composition may, in addition to the conjugate of the invention with a specific activity, further comprise other enzyme activities e.g. also in the form of an enzyme conjugate as described according to the present invention, providing cleaning performance and/or fabric care benefits, e.g. proteases, lipases, cutinases, amylases, cellulases, peroxidases, oxidases (e.g. laccases).

Specific examples of contemplated enzymes are listed above in the section "The enzyme activity".

Bleaching Agents:

The detergent composition (especially in the case of a granular detergent) may also comprise a bleaching agents, e.g. an oxygen bleach or a halogen bleach. The oxygen bleach may be a hydrogen peroxide releasing agent such as a perborate (e.g. PB1 or PB4) or a percarbonate, or it may e.g. be a percarboxylic acid. The particle size may be 400–800 microns. When present, oxygen bleaching compounds will typically be present at levels of from about 1% to about 25%.

The hydrogen peroxide releasing agent can be used in, combination with bleach activators such as tetraacetylethylenediamine (TAED), nonanoyloxybenzene-sulfonate (NOBS), 3,5-trimethyl-hexsanoloxybenzene-sulfonate (ISONOBS) or pentaacetylglucose (PAG).

The halogen bleach may be, e.g. a hypohalite bleaching agent, for example, trichloro isocyanuric acid and the sodium and potassium dichloroisocyanurates and N-chloro and N-bromo alkane sulphonamides. Such materials are normally added at 0.5–10% by weight of the finished product, preferably 1–5% by weight.

Textile Applications

Proteases

Proteases are used for degumming and sand-washing of silk.

Lipases

Lipases are used for removing fatty matter containing hydro phobic esters (e.g. triglycerides) during the finishing of textiles (see e.g. WO 93/13256 from Novo Nordisk A/S).

Oxidoreductases

In bleach clean-up of textiles catalases may serve to remove excess hydrogen peroxide.

Carbohydrases

Cellulolytic enzymes are widely used in the finishing of denim garments in order to provide a localized variation in the colour density of the fabric (Enzyme facilitated "stone wash").

Also cellulolytic enzymes find use in the bio-polishing process. Bio-Polishing is a specific treatment of the yarn surface which improves fabric quality with respect to handle and appearance without loss of fabric wettability. Bio-polishing may be obtained by applying the method described e.g. in WO 93/20278.

During the weaving of textiles, the threads are exposed to considerable mechanical strain. In order to prevent breaking, they are usually reinforced by coating (sizing) with a gelatinous substance (size). The most common sizing agent is starch in native or modified form. A uniform and durable finishing can thus be obtained only after removal of the size from the fabric, the so called desizing. Desizing of fabrics sized with a size containing starch or modified starch is preferably facilitated by use of amylolytic enzymes.

Food and Feed Applications

Conjugated enzymes or polypeptides of the invention may advantageously be used in the manufacturing of food and feed.

Proteases

The gluten in wheat flour is the essential ingredient responsible for the ability of flour to be used in baked foodstuffs. Proteolytic enzymes are sometimes needed to modify the gluten phase of the dough, e.g. a hard wheat flour can be softened with a protease.

Neutrase® is a commercially available neutral metalloprotease that can be used to ensure a uniform dough quality and bread texture, and to improve flavour. The gluten proteins is degraded either moderately or more extensively to peptides, whereby close control is necessary in order to avoid excessive softening of the dough.

Proteases are also used for modifying milk protein.

To coagulate casein in milk when producing cheese proteases such as rennet or chymosin may be used.

In the brewery industry proteases are used for brewing with unmalted cereals and for controlling the nitrogen content.

In animal feed products proteases are used so to speak to expand the animals digestion system.

Lipases

The application of lipase in the baking industry is rather new. Addition of lipase results in improved dough properties and an improved breadmaking quality in terms of larger volume, improved crumb structure and whiter crumb colour. The observed effect can be explained by a mechanism where the lipase-changes the interaction between gluten and some lipids fragment during dough mixing. This results in an improved gluten network.

The flavour development of blue roan cheeses (e.g. Danablue), certain Italian cheese types and other dairy products containing butter fat are dependent on the degradation of milk fat into free fatty acids. Lipases may be used for developing flavour in such products.

In the oil- and fat producing industry lipases are used e.g. to minimize the amount of undesirable side-products, to modify fats by interesterification, and to synthesis of esters.

Oxidoreductases

Further oxidoreductases with reduced allergenicity according to the invention may advantageously be used in the manufacturing of food and feed.

Several oxidoreductases are used for baking, glucose oxidase, lipoxygenase, peroxidase, catalase and combinations hereof. Traditionally, bakers strengthen gluten by adding ascorbic acid and potassium bromate. Some oxidoreductases can be used to replace bromate in dough systems by oxidation of free sulfydryl units in gluten proteins. Hereby disulphide linkages are formed resulting in stronger, more elastic doughs with greater resistance.

Gluzyme® (Novo Nordisk A/S) is a glucose oxidase preparation with catalase activity that can be used to replace bromate. The dough strengthen is measured as greater resistance to mechanical shock, better oven spring and larger loaf volume.

Carbohydrases

Flour has varying content of amylases leading to differences in the baking quality. Addition of amylases can be necessary in order to standardize the flour. Amylases and pentosanases generally provide sugar for the yeast fermentation, improve the bread volume, retard retrogradation, and decrease the staling rate and stickiness that results from pentosan gums. Examples of carbohydrases is given below.

Certain maltogenic amylases can be used for prolonging the shelf life of bread for two or more days without causing gumminess in the product. Selectively modifies the gelatinized starch by cleaving from the non-reducing end of the starch molecules, low molecular weight sugars and dextrins. The starch is modified in such a way that retrogradation is less likely to occur. The produced low-molecular-weight sugars improve the baked goods water retention capacity without creating the intermediate-length dextrins that result in gumminess in the finished product. The enzyme is inactivated during bread baking, so it can be considered a processing aid which does not have to be declared on the label. Overdosing of Novamyl can almost be excluded.

The bread volume can be improved by fungal α-amylases which further provide good and uniform structure of the bread crumb. Said α-amylases are endoenzymes that produce maltose, dextrins and glucose. Cereal and some bacterial α-amylases are inactivated at temperatures above the gelatinization temperature of starch, therefore when added to a wheat dough it results in a low bread volume and a sticky bread interior. Fungamyl has the advantage of being thermolabile and is inactivated just below the gelatinization temperature.

Enzyme preparations containing a number of pentosanase and hemi-cellulase activities can improve the handling and stability of the dough, and improves the freshness, the crumb structure and the volume of the bread.

By hydrolysing the pentosans fraction in flour, it will lose a great deal of its water-binding capacity, and the water will then be available for starch and gluten. The gluten becomes more pliable and extensible, and the starch gelatinize more easily. Pentosanases can be used in combination with or as an alternative to emulsifiers.

Further carbohydrases are used for producing syrups from starch, which are widely used in soft drinks, sweets; meat products, dairy products, bread products, ice cream, baby food, jam etc.

The conversion of starch is normally carried out three steps.

First the starch is liquefied, by the use of α-amylases. Maltodextrins, primary consisting of oligosaccharides and dextrins, are obtained.

The mixture is then treated with an amyloglucosidase for hydrolysing the oligosaccharides and dextrins into glucose. This way a sweeter product is obtained. If high maltose syrups are desired b-amylases alone or in combination with a pullulanase (de-branching enzyme) may be used.

The glucose mixture can be made even sweeter by isomerization to fructose. For this an immobilized glucose isomerase can be used.

In the sugar industry, it is common practice to speed up the break down of present starch in cane juices. Thereby the starch content in the raw sugar is reduced and filtration at the refinery facilitated.

Furthermore dextranases are used to break down dextran in raw sugar juices and syrups.

In the alcohol industry a-amylases are advantageously being used for thinning of starch in distilling mashes.

In the brewing industry a-amylases are used for adjunct liquefaction.

In the dairy industry b-galactosidases (lactase) is used when producing low lactose milk for persons suffering from lactose malabsorption.

When flavoured milk drinks are produced from lactase-treated milk, the addition of sugar can be reduced without reducing the sweetness of the product.

In the production of condensed milk, lactose crystallization can be avoided by lactase treatment, and the risk of thickening caused by casein coagulation in lactose crystals is thus reduced.

When producing ice cream made from lactase-treated milk (or whey) no lactose crystals will be formed and the defect, sandiness, will not occur.

Further, xylanases are known to be used within a number of food/feed industrial applications as described in WO 94/21785 (Novo Nordisk A/S).

α-amylases are used in the animal feed industry to be added to cereal-containing feed to improve the digestibility of starch.

Anti-microbial Polypeptides

Certain bacteriolytic enzymes may be used e.g. to wash carcasses in the meat packing industry (see U.S. Pat. No. 5,354,681 from Novo Industri A/S).

Transferases

Transglutaminases with reduced allergenicity according to the invention may advantageously be used in the manufacturing of food and feed.

Transglutaminases has the ability to crosslinking protein.

This property can be used for gelling of aqueous phases containing proteins. This may be used for when producing of spreads (wo 96/08156 from Novo Nordisk A/S).

Transglutaminases are being used for improvement of baking quality of flour e.g. by modifying wheat flour to be used in the preparation of cakes with improved properties, such as improved taste, dent, mouth-feel and a higher volume (see JP 1-110147).

Further producing paste type food material e.g. used as fat substitution in foods as ice cream, toppings, frozen desserts, mayonnaises and low fat spreads (see WO 93/22930 from Novo Nordisk A/S).

Furthermore for preparation of gels for yoghurt, mousses, cheese, puddings, orange juice, from milk and milk-like products, and binding of chopped meat product, improvement of taste and texture of food proteins (see WO 94/21120 and WO 94/21129 from Novo Nordisk A/S).

Phytases

Phytases of the invention may advantageously be used in the manufacturing of food, such as breakfast cereal, cake, sweets, drink, bread or soup etc., and animal feed.

Phytases may be used either for exploiting the phosphorus bound in the phytate/phytic acid present in vegetable protein sources or for exploiting the nutritionally important minerals bound in phytic acid complexes.

Microbial phytase may be added to feedstuff of monogastric animals in order to avoid supplementing the feed with inorganic phosphorus (see U.S. Pat. No. 3,297,548)

Further phytases may be used in soy processing. Soyabean meal may contain high levels of the anti-nutritional factor phytate which renders this protein source unsuitable for application in baby food and feed for fish, calves and other non-ruminants, since the phytate chelates essential minerals present therein (see EP 0 420 358).

Also for baking purposes phytases may be used. Bread with better quality can be prepared by baking divided pieces of a dough containing wheat flour etc. and phytase (see JP-0-3076529-A).

A high phytase activity koji mold are known to be used for producing refined sake (see JP-0-6070749-A).

MATERIAL AND METHODS

Materials

Enzymes:

PD498: Protease of subtilisin type shown in WO 93/24623. The sequence of PD498 is shown in SEQ ID NO: 1 and 2.

Subtilisin DY: Protease of the subtilisin type shown in SEQ ID NO: 3 isolated from Bacillus sp. variant (Betzel et al. (1993), Archives of Biophysics, Vol. 302, No. 2, p. 499–502).

ELISA Reagents:

Horse Radish Peroxidase labelled pig anti-rabbit-Ig (Dako, DK, P217, dilution 1:1000).

Rat anti-mouse IgE (Serotec MCA419; dilution 1:100).
Mouse anti-rat IgE (Serotec MCA193; dilution 1:200).

Biotin-labelled mouse anti-rat IgG1 monoclonal antibody (Zymed 03-9140; dilution 1:1000)

Biotin-labelled rat anti-mouse IgG1 monoclonal antibody (Serotec MCA336B; dilution 1:2000)

Streptavidin-horse radish peroxidase (Kirkegard & Perry 14-30-00; dilution 1:1000).

| Buffers and Solutions: | |
|---|---|
| PBS (pH 7.2 (1 liter)) | |
| NaCl | 8.00 g |
| KCl | 0.20 g |
| K2HPO4 | 1.04 g |
| KH2PO4 | 0.32 g |
| Washing buffer PBS, 0.05% (v/v) Tween 20 | |
| Blocking buffer PBS, 2% (wt/v) Skim Milk powder | |
| Dilution buffer PBS, 0.05% (v/v) Tween 20, 0.5% (wt/v) Skim Milk powder | |
| Citrate buffer (0.1M, pH 5.0–5.2 (1 liter)) | |
| NaCitrate | 20.60 g |
| Citric acid | 6.30 g |

Stop-solution (DMG-buffer)
Sodium Borate, borax (Sigma)
3,3-Dimethyl glutaric acid (Sigma)
$CaCl_2$ (Sigma)
Tween 20: Poly oxyethylene sorbitan mono laurate (Merck cat no. 822184)

N-Hydroxy succinimide (Fluka art. 56480))
Phosgene (Fluka art. 79380)
Lactose (Merck 7656)
PMSF (phenyl methyl sulfonyl flouride) from Sigma
Succinyl-Alanine-Alanine-Proline-Phenylalanine-para-nitroanilide (Suc-AAPF-pNP) Sigma no. S-7388, Mw 624.6 g/mole.
mPEG (Fluka)
Colouring Substrate:
OPD: o-phenylene-diamine, (Kementec cat no. 4260)
Test Animals:
Brown Norway rats (from Charles River, Del.)
Equipment:
XCEL II (Novex)
ELISA reader (UVmax, Molecular Devices)
HPLC (Waters)
PFLC (Pharmacia)
Superdex-75 column, Mono-Q, Mono S from Pharmacia, SW.
SLT: Fotometer from SLT LabInstruments
Size-exclusion chromatograph (Spherogel TSK-G2000 SW).
Size-exclusion chromatograph (Superdex 200, Pharmacia, SW)
Amicon Cell

Methods

Intratracheal (IT) Stimulation of Brown Norway Rats

For IT administration of molecules disposable syringes with a 2½" long metal probe is used. This probe is instilled in the trachea of the rats approximately 1 cm below the epiglottis, and 0.1 ml of a solution of the molecules is deposited.

The test animals are Brown Norway rats (BN) in groups of 10. Weight at time of start is more than 200 grams and at termination approximately 450 grams.

ELISA Procedure to Determine Relative Concentrations of IgE Antibodies in Brown Norway Rats.

A three layer sandwich ELISA is used to determine relative concentrations of specific IgE serum anti-bodies.

1) Coat the ELISA-plate with 10 mg mouse anti-rat IgE Buffer 1 (50 microL/well). Incubate over night at 4° C.

2) Empty the plates and block with Blocking buffer for at least ½ hour at room temperature (200 microL/well). Shake gently. Wash the plates 3 times with Washing Buffer.

3) Incubate with rat sera (50 microL/well), starting from undiluted and continue with 2-fold dilutions. Keep some wells free for buffer 4 only (blanks). Incubate for 30 minutes at room temperature. Shake gently. Wash the plates 3 times in Washing Buffer.

4) Dilute the enzyme in Dilution buffer to the appropriate protein concentration.

Incubate 50 microL/well for 30 minutes at room temperature. Shake gently. Wash the plates 3 times in Washing Buffer.

5) Dilute specific polyclonal anti-enzyme antiserum serum (pIg) for detecting bound antibody in Dilution buffer. Incubate 50 microl/well for 30 minutes at room temperature. Shake gently. Wash the plates 3 times in Washing Buffer.

6) Dilute Horseradish Peroxidase-conjugated anti-pIg-antibody in Dilution buffer. Incubate 50 microL/well at room temperature for 30 minutes. Shake gently. Wash the plates 3 times in Washing Buffer.

7) Mix 0.6 mg ODP/ml+0.4 microL $H_2O_2$/ml in substrate Buffer. Make the solution just before use. Incubate for 10 minutes. 50 microL/well.

8) To stop the reaction, add 50 microL Stop Solution/well.

9) Read the plates at 492 nm with 620 nm as reference. Data is calculated and presented in Lotus.

Determination of the Molecular Weight

Electrophoretic separation of proteins was performed by standard methods using 4–20% gradient SDS polyacrylamide gels (Novex). Proteins were detected by silver staining. The molecular weight was measured relatively to the mobility of Mark-12® wide range molecular weight standards from Novex.

Protease Activity

Analysis with Suc-Ala-Ala-Pro-Phe-pNa:

Proteases cleave the bond between the peptide and p-nitroaniline to give a visible yellow colour absorbing at 405 nm.

Buffer: e.g. Britton and Robinson buffer pH 8.3 Substrate: 100 mg suc-AAPF-pNa is dissolved into 1 ml dimethyl sulfoxide (DMSO). 100 ml of this is diluted into 10 ml with Britton and Robinson buffer.

Analysis

The substrate and protease solution is mixed and the absorbance is monitored at 405 nm as a function of time and $ABS_{405\ nm}$/min. The temperature should be controlled (20–50° C. depending on protease). This is a measure of the protease activity in the sample.

EXAMPLES

Example 1

Activation of mPEG 350 with N-succinimidyl Carbonate mPEG 350 was dissolved in toluene (4 ml/g of mPEG). About 20% was distilled off at normal pressure to dry the reactants azeotropically. The solution was cooled to 20° C. and phosgene in toluene (1.93 M 1.5 mole/mole mPEG) was added. The mixture was then stirred at room temperature over night. The mixture was evaporated under reduced pressure and the intermediate chloroformate was obtained as an oil.

After evaporation dichloromethane and toluene (1:2, dry 4 ml/g mPEG) was added to re-dissolve the colorless oil. N-Hydroxy succinimide (NHS) (1.5 mole/mole mPEG.) was added as a solid and then triethylamine (1.1 mole/mole mPEG) at 0° C. Immediate precipitation of triethylamine hydrochloride ($Et_3N.HCl$) could be observed. The mixture was stirred overnight at room temperature. The mixture was filtered using a glass frit (G5) to remove the $Et_3N.HCl$. The filtrate was evaporated to dryness under reduced pressure to yield 98% (mole/mole) of an oil. NMR Indicating 85–95% activation and <10 o/o (mole/mole) $HNEt_3Cl$. $^1H$-NMR for mPEG 350 succinimidylcarbonate ($CDCl_3$) d 1.42 t (I=1.4 $CH_3$ in $HNEt_3Cl$), 2.68 s (I=3.4 unreacted NHS), 2.84 s (I=6.2 succinimide), 3.10 dq (I=1.0 $CH_2$ i $HNEt_3Cl$), 3.38 s (I=5.8 $CH_3$ i OMe), 3.64 bs (I=50 main peak), 4.47 t (I=3.0, $CH_2$ in PEG).

Example 2

Conjugation of PD498 Protease with Activated mPEG 350

62 mg of PD498 was incubated in 50 mM Sodium Borate, pH 9.7, with 20 mg (≈200 μl) of activated mPEG 350 with N-succinimidyl carbonate (prepared according to Example 1), in a final volume of 6 ml. The reaction was carried out at ambient temperature using magnetic stirring. Reaction time was 2 hour. The reaction was stopped by adding 0.5 M succinic acid to a final pH of 6.0.

The molecular weight of the obtained derivative was approximately 33 kDa, corresponding to about 11 moles of mPEG attached per mole PD498.

Compared to the parent enzyme, residual activity was close to 100% towards peptide substrate (succinyl-Ala-Ala-Pro-Phe-p-Nitroanilide).

Example 3

Conjugation of Subtilisin DY Protease with Activated mPEG 350

Subtilisin DY was conjugated to mPEG 350 with N-succinimidyl carbonate using the same procedure as described in Example 2.

As will be apparent to those skilled in the art, in the light of the foregoing disclosure, many alterations and modifications are possible in the practice of this invention without departing from the spirit or scope thereof. Accordingly, the scope of the invention is to be construed in accordance with the substance defined by the following claims.

Example 4

Brown Norway Rat Intratrachaeal (IT) Trials of PD498 Conjugates of Small mPEG Polymers PD498 samples with known protein concentration (measured by optical density and amino acid sequence analysis for derivatives) were diluted to 0.75 microG protein/ml.

The diluted samples were aliquoted in 1.5 ml fractions for individual immunizations. These fractions were stored under stable conditions at −20° C. until use. The analyses were performed at the beginning and at the end of the study. For each immunization and each analysis a new fraction was taken.

Enzyme conjugates were conjugated with N-succinimidyl carbonate activated mPEG 350, 550, 750 as described in the examples above. The corresponding parent enzymes were used as controls.

The following samples were tested:

Group 1: PD498 (parent uncoupled enzyme—control)
Group 2: PD498-SPEG 750
Group 3: PD498-SPEG 550
Group 4: PD498-SPEG 350

Rats were immunized weekly 15 times with 100 microL of a 0.9% (wt./vol.) NaCl solution (control group), or 100 microL of the PD498 protein dilutions mentioned above.

Each group comprised 10 Brown Norway rats. Blood samples (2 ml) were collect from the eyes one week after every second immunization, but before the following immunization. Serum was obtained by blood clotting, and centrifugation.

Specific IgE levels were determined using the ELIAS assay specific for rat IgE described above. The sera were titrated at ½ dilution, starting from undiluted. Optical density was measured at 492/620 nm.

The result of the IT trials are shown in the following table illustrating the total optical density per 100 microL of serum at the end of the study, as observed in Brown Norway rats with the respective PD498 derivatives.

The result of the PD498 conjugate trials is shown in Table 1 below:

TABLE 1

| # of immuni-zations | un-modified | PEG 350 | PEG 550 | PEG 750 | NaCl |
|---|---|---|---|---|---|
| 0 | 0.3 | 0.3 | 0.3 | 0.3 | 0.3 |
| | (0.6) | (0.6) | (0.6) | (0.6) | (0.6) |
| 15 | 5.3 | 2.7 | 1.6 | 1.5 | 0.3 |
| | (1.6) | (1.2) | (0.6) | (1.4) | (0.6) |

Value in parenthesis: Standard error of the mean value determined.

As can be seen from the Table 1 the specific IgE response level of the rats exposed intratracheally with the PD498 conjugate with small polymers coupled thereto is reduced in comparison to rats having been exposed intratracheally with the parent unmodified enzymes. Thus, the allergenicity is reduced.

Example 5
Brown Norway Rat Intratrachaeal (IT) Trials of a Subtilisin DY Conjugate The Brown Norway rat IT study described in Example 4 was repeated comparing a Subtilisin DY-SPEG750 conjugate with the corresponding parent Subtilisin DY enzyme (see SEQ ID NO: 3)

The result of the Subtilisin DY-SPEG750 trial is shown in table 2:

TABLE 2

| # of immuni-zations | un-modified | PEG 750 | NaCl |
|---|---|---|---|
| 0 | 0.3 (0.6) | 0.3 (0.6) | 0.3 (0.6) |
| 15 | 7.2 (2.0) | 1.9 (0.4) | 0.3 (0.6) |

Value in parenthesis: standard error of the mean value determined As can be seen from the Table 2 the specific IgE response level of the rats exposed intratracheally with the Subtilisin DY conjugate with a 750 Da polymer coupled thereto is reduced in comparison to rats having been exposed intratracheally with the parent unmodified enzyme.

Thus, the allergenicity is reduced.

Example 6
Skin Care Formulations Comprising a PD498-SPEG Conjugate

The following skin care formulations comprising conjugates of the invention were prepared:

| Lotion (to make 100 g) | |
|---|---|
| Oil phase: | |
| Liquid Paraffin | 35 g |
| Cetyl Alcohol | 5 g |
| Tween 80 | 7 g |
| Water phase: | |
| Mono Propylene Glycol (MPG) | 10 g |
| 0.4% citric acid buffer* pH 5.8 | 42.9 g |
| Methyl Paraben | 0.1 g |
| PD498-SPEG550 ** (as enzyme protein) | 10 mg |

*0.4% citric acid monohydrate, pH adjusted to 5.9
** Will usually be supplied as a formulation with MPG. MPG in the water phase should be adjusted according to the amount of MPG in the enzyme formulation.

The Oil phase and the water phase were mixed separately and heated to 80° C. The oil phase was poured slowly into the water phase while stirring. The mixture was cooled to apprx. 35 C. and the PD498-SPEG550 conjugate was added. The lotion was cooled rapidly.

| Gel (to make 100 g) | |
|---|---|
| MPG | 20 g* |
| H2O | ad. 100 g |
| Citric Acid | 0.4 g** |
| Carbapol 940 | 1 g |
| PD498-SPEG350 (as enzyme protein) | 10 mg |

*Adjust according to amount in enzyme formulation.
**pH 5.6

The ingredients were mixed in the above order. The pH was adjusted to 5.6 before addition of carbapol. After addition of carbapol the pH was adjusted again.

What is claimed is:

1. A method of using a polypeptide, comprising industrial application of a polypeptide modified by conjugation to one or more polymeric molecules, wherein the polymeric molecule(s) have a molecular weight of from 100 to 750 Da and the polypeptide has a molecular weight of from 5 to 100 kDa.

2. The method of claim 1, wherein the industrial application of the polypeptide is as a detergent, household article product, agrochemical, personal care product, method used for treating/processing textiles, method for hard surface cleaning, or method used for manufacturing food and feed.

3. The method of claim 1, wherein the industrial application of the polypeptide is as a food or feed additive.

4. The method of claim 1, wherein the industrial application of the polypeptide is as a skin care product or detergent.

5. The method of claim 1, wherein the molecular weight of the polymeric molecule(s) is from 100 to 500 Da.

6. The method of claim 5, wherein the molecular weight of the polymeric molecule(s) is from 100 to 350 Da.

7. The method of claim 6, wherein the molecular weight of the polymeric molecule(s) is from 100 to 300 Da.

8. The method of claim 1, wherein the polypeptide is an enzyme having a molecular weight from 15 to 60 kDa.

9. The method of claim 1, wherein from 1 to 100 polymeric molecules are coupled covalently to the polypeptide.

10. The method of claim 9, wherein from 4 to 50 polymeric molecules are coupled covalently to the polypeptide.

11. The method of claim 10, wherein from 5 to 35 polymeric molecules are coupled covalently to the polypeptide.

12. The method of claim 1, wherein the polymeric molecule(s) are natural or synthetic homopolymer(s) or heteropolymer(s).

13. The method of claim 1, wherein the polymeric molecule(s) are polyols, polyamines or polycarboxyl acids.

14. The method of claim 1, wherein the polymeric molecule(s) are polyalkylene oxides (PAO), methoxypolyethylene glycols (mPEG) and polypropylene glycols, PEG-glycidyl ethers (Epox-PEG), PEG-oxycarbonylimidazole (CDI-PEG), branched PEGs, poly-vinyl alcohol (PVA), poly-carboxylates, poly-(vinylpyrolidone), poly-D,L-amino acids, polyethylene-co-maleic acid anhydride, polystyrene-co-malic acid anhydride, dextrans, heparin, homologous albumin, celluloses, hydrolysates of chitosan, starches, glycogen, agaroses or a derivative thereof, guar gum, pullulan, inulin, xanthan gum, carrageenan, pectin, alginic acid hydrolysates or bio-polymers.

15. The method of claim 1, wherein the polymeric molecule(s) are branched polyethylene glycols (PEG), poly-vinyl alcohol (PVA), polycarboxyl acids, polyvinylpyrrolidone or poly-D,L-amino acids.

16. The method of claim 1, wherein the polymeric molecule(s) are dextrans, celluloses, hydrolysates of chitosan, starches, glycogen, agarose, guar gum, inulin, pullulans, xanthan gums, carrageenin, pectin or alginic acid.

17. The method of claim 1, wherein the polymeric molecule(s) are polyalkylene glycols (PAG).

18. The method of claim 1, wherein the polymeric molecule(s) are polyethylene glycols (PEG).

19. The method of claim 1, wherein the polymeric molecule(s) are carboxymethyldextrans.

20. The method of claim 1, wherein the polymeric molecule(s) are methylcellulose, carboxymethylcellulose, ethylcellulose, hydroxyethylcellulose, carboxyethylcellulose or hydroxypropylcellulose.

21. The method of claim 1, wherein the polymeric molecule(s) are hydroxyethyl-starches or hydroxy propyl-starches.

22. The method of claim 1, wherein the polymeric molecule(s) are methoxypolyethylene glycols (mPEG).

23. The method of claim 1, wherein the polymeric molecule(s) are bis-OH polyethylene glycols.

24. The method of claim 1, wherein the polypeptide is of microbial origin.

25. The method of claim 1, wherein the polypeptide is a hydrolase.

26. The method of claim 1, wherein the polypeptide is an oxidoreductase.

27. The method of claim 26, wherein the polypeptide is a laccase.

28. The method of claim 26, wherein the polypeptide is a peroxidase.

29. The method of claim 1, wherein the polypeptide is a protease.

30. The method of claim 1, wherein the polypeptide is a lipase.

31. The method of claim 1, wherein the polypeptide is a transglutaminase.

32. The method of claim 1, wherein the polypeptide comprises one of SEQ ID NO:2, SEQ ID NO:3, SEQ ID NO:4 or SEQ ID NO:5.

* * * * *